United States Patent [19]

Wilson, Jr. et al.

[11] Patent Number: 4,593,129

[45] Date of Patent: Jun. 3, 1986

[54] POLYPHOSPHAZENE PROCESS

[75] Inventors: R. Woodrow Wilson, Jr.; Dustin H. Thomas, both of Baton Rouge, La.

[73] Assignee: Ethyl Corporation, Richmond, Va.

[21] Appl. No.: 601,505

[22] Filed: Apr. 18, 1984

[51] Int. Cl.$^4$ .............................................. C07C 2/56
[52] U.S. Cl. ................... 568/716; 568/662; 568/706; 568/774; 568/780; 568/840; 568/841; 568/812
[58] Field of Search ............... 568/715, 716, 812, 840, 568/706, 662, 774, 780, 841, 735; 260/973

[56] References Cited

U.S. PATENT DOCUMENTS

| | | | |
|---|---|---|---|
| 3,515,688 | 6/1970 | Rose et al. | 423/300 |
| 3,700,629 | 10/1972 | Reynard et al. | 260/97 P |
| 3,702,833 | 11/1972 | Rose et al. | 423/302 |
| 3,732,175 | 5/1973 | Allcock | 423/97 |
| 3,838,073 | 9/1974 | Rose et al. | 423/300 |
| 3,844,983 | 10/1974 | Reynard et al. | 423/302 |
| 3,888,799 | 6/1975 | Rose | 423/302 |
| 3,888,800 | 6/1975 | Rose | 423/302 |
| 3,896,058 | 7/1975 | Reynard et al. | 423/302 |
| 3,943,088 | 3/1976 | Kyker et al. | 423/302 |
| 3,945,966 | 3/1976 | Vicic et al. | 423/300 |
| 3,948,820 | 4/1976 | Reynard | 423/302 |
| 3,970,533 | 7/1976 | Kyker et al. | 204/159.14 |
| 3,972,841 | 8/1976 | Cheng | 526/246 |
| 4,000,166 | 12/1976 | Witner et al. | 423/300 |

FOREIGN PATENT DOCUMENTS

| | | | |
|---|---|---|---|
| 28963 | 7/1972 | Japan | 568/716 |
| 795440 | 5/1958 | United Kingdom | 568/715 |

Primary Examiner—Werren B. Lone
Attorney, Agent, or Firm—Donald L. Johnson; John F. Sieberth; Joseph D. Odenweller

[57] ABSTRACT

A process for making an alkali metal alkoxide (e.g. sodium alkoxide) of a halogen-substituted alcohol (e.g. fluorine-substituted alcohols) by dispersing an alkali metal (e.g. sodium) in a cycloalkane (e.g. cyclohexane) containing a phenol (e.g. o-allylphenol) and adding the resultant dispersion to an ether (e.g. THF) solution of a halogen-substituted alcohol. The resultant alkali metal haloalkoxide solution contains phenoxides and can be reacted with a phosphonitrilic chloride polymer to introduce haloalkoxide and phenoxide substituents.

12 Claims, No Drawings

POLYPHOSPHAZENE PROCESS

BACKGROUND OF THE INVENTION

Haloalkoxide-substituted phosphazene polymers are useful in many applications because of their flame resistance, low temperature flex properties and high temperature stability. Of these, most interest has been in the fluoroalkoxide-substituted polyphosphazene. Such compositions are disclosed in U.S. Pat. Nos. 3,515,688 and 3,700,629. Other fluoroalkoxides-substituted phosphazene polymers are disclosed in U.S. Pat. Nos. 3,702,833, 3,732,175, 3,838,073, 3,844,983, 3,888,799, 3,888,800, 3,896,058, 3,943,088, 3,945,966, 3,948,820, 3,970,533, 3,972,841, 4,000,166, all of which are incorporated herein by reference for their disclosure of the prior methods of making alkaline metal fluoroalkoxides and the use of such fluoroalkoxides in preparing polyphosphazene polymers and the utility of such polyphosphazene polymers.

In U.S. Pat. No. 3,515,688, the sodium fluoroalkoxide used to make the fluoroalkoxide-substituted phosphazene polymers was prepared by reacting metallic sodium directly with the fluorine-substituted alcohol. Pieces of metallic sodium, which were cut and weighed under dried benzene, were added directly to the fluorine-substituted alcohol and the mixture stirred overnight following which it was refluxed to complete the reaction. A hazard associated with a process carried out in this manner is that the metallic sodium in addition to reacting with the alcohol hydroxyl groups can also react with the halogen bonded to the alcohol. Such reactions can become very exothermic and lead to eruption of the reaction contents from the reaction vessel and can ignite. Attempts to prepare sodium alkoxides of fluorine-substituted alcohols using sodium dispersed in toluene were not successful because the sodium dispersion initially made in toluene tended to coalesce.

Fluoroalkoxide-substituted polyphosphazenes containing a few random o-allylphenoxide substituents are described in Kyker, et al, U.S. Pat. No. 3,970,533. The allylphenoxide groups impart cross-linking properties to the elastomer permitting them to be cured using curing agents such as peroxide or sulfur. Kyker, et al made these products by adding a mixture of fluoroalcohols and o-allylphenol to sodium metal in dry tetrahydrofuran. The sodium fluoroalkoxide o-allylphenoxide solution which resulted was added to a benzene solution of linear phosphonitrilic chloride polymer.

SUMMARY OF THE INVENTION

It has now been discovered that sodium dispersions made in a cycloalkane such as cyclohexane containing a phenol retain their dispersed state and when added in a controlled manner to a fluorine-substituted alcohol react rapidly with the alcoholic hydroxyl group without accummulating large amounts of unreacted sodium which could lead to the hazard referred to above. The sodium fluoroalkoxide-phenoxide mixture prepared in this manner reacts very efficiently with phosphonitrilic chloride polymers thereby replacing the chlorine atoms with fluoroalkoxide and phenoxide groups.

DESCRIPTION OF THE PREFERRED EMBODIMENTS

A preferred embodiment of the invention is a process for making a mixture of a sodium alkoxide of a halogen-substituted alcohol and a sodium aryloxide of a phenol without excessive reaction of sodium with the halogen substituent, said process comprising (a) dispersing about one equivalent of molten metallic sodium in a cycloalkane hydrocarbon containing about 5-8 carbon atoms and 0.05-0.5 moles of a phenol at a pressure high enough to maintain said cycloalkane hydrocarbon in the liquid phase above the melting temperature of sodium;

(b) cooling the resultant dispersion to a temperature below the melting point of sodium; and (c) adding the resultant dispersion to a solution of of a halogen-substituted alcohol in an ether solvent at a temperature of about $-30°$ C. up to reflux the amount of halogen-substituted alcohol being sufficient to react with at least a major amount of the metallic sodium in the resultant dispersion.

Preferred cycloalkane useful in the process are those containing about 5-8 carbon atoms such as cyclopentane, cyclohexane, cycloheptane and cyclooctane. The cycloalkane ring may be substituted with alkyl groups such as methyl, ethyl, propyl and the like. The preferred cycloalkane hydrocarbon is cyclohexane.

A broad range of phenols can be used to make the dispersion. Examples include phenol, o-cresol, p-cresol, m-ethylphenol, p-ethylphenol, p-isopropylphenol, p-sec-butylphenol, p-tert-octylphenol, p-n-dodecylphenol, p-sec-eicosylphenol, $\alpha$-naphthol, $\beta$-naphthol, p-methoxyphenol, m-ethoxyphenol, and the like.

The more preferred phenols are the allyl-substituted phenols. These phenols introduce allylphenoxide groups into the sodium dispersion. When the resultant sodium dispersion is used to make haloalkoxides, the mixture will also contain allylphenoxides. When this mixture is subsequently used to substitute a phosphonitrilic chloride polymer, it will introduce both haloalkoxide and allylphenoxide groups. The allylphenoxide groups are beneficial in that they impart curing properties to the resultant polyphosphazene.

Allylphenols are aromatic hydroxy compounds having an allyl group bonded to a benzene ring. Although mononuclear aromatics are preferred, the invention includes the use of allyl-substituted polynuclear phenols. Examples of suitable allylphenols include o-allyl-p-cresol, 2-allyl-4-ethylphenol, 4-allylphenol, 2-methyl-4-allylphenol, 2-allyl-4-chloro-phenol, 2-allyl-4-fluorophenol, 2-allyl-4,6-difluorophenol, 2-allyl-4-isopropylphenol, 2-allyl-1-naphthol, 4-allyl-1-naphthol, 4-allyl-2-naphthol, 2-allyl-4-methoxyphenol, 2-allyl-4-ethoxyphenol, 2,4-diallylphenol, 2-allyl-4-nitrophenol, and the like. The most preferred allylphenol is ortho-allylphenol.

The amount of phenol in the cycloalkane need not be great. A range of about 0.01-0.2 gram moles per each gram atom or equivalent of sodium is a useful range. In most cases, an excellent dispersion is obtained using about 0.05-0.2 moles of phenol per equivalent of sodium. The phenol can be added to the cycloalkane prior to adding the sodium metal. Alternatively, it can be added after adding the sodium metal. Likewise, it can be added after heat-up to melt the sodium or even after the molten sodium is agitated to form the dispersion.

Alkali metals that can be used in the process include both sodium and potassium. Of these, sodium is most preferred because of its ready availability and low cost. The amount of sodium in the dispersion can vary over a wide range. A preferred concentration is from about 20-50 weight percent sodium in the resultant sodium dispersion. A more preferred sodium concentration is from about 30 to 40 weight percent.

The dispersion is prepared by adding metallic sodium to the cycloalkane hydrocarbon containing a phenol and heating the mixture to a temperature above the melting point of sodium and maintaining at this temperature until the sodium becomes molten. Sodium melts at about 97.5° C. which is above the normal boiling point of cyclopentane and cyclohexane. When the temperature used to make the dispersion is above the normal boiling point of the cycloalkane dispersion medium pressure equipment must be used to prepare the dispersion. Only modest pressures are encountered. For example, using cyclohexane at 105° C. resulted in a pressure of 14 psig.

Optionally, the sodium can be pre-melted and added to the hot cycloalkane containing a phenol in order to reduce processing time.

The sodium used in the process should be cleaned of oxides and hydroxides which frequently form on the surface of metallic sodium. The dispersing temperature is preferably about 105°–120° C. although temperatures as low as 100° C. can be used. The dispersion is then formed by vigorously agitating the mixture using a high shear dispersing agitator such as a conventional turbine type dispersing head. Such dispersing heads are used at very high RPM such that the tip speed of the agitator is in the vicinity of 45–90 feet per second.

Halogen-substituted alcohols which can be reacted to form sodium alkoxides according to the present process include any halogen-substituted alcohol and can contain up to 20 or more carbon atoms and 41 or more halogen atoms. Halogen substituents include chlorine, fluorine, bromine and iodine. Examples of such halogen-substituted alcohols are trifluoromethanol, trichloromethanol, 2-chloro-ethanol, 2,2-dichloroethanol, 2,2-difluoroethanol, 2,2-dibromoethanol, 2,2,2-trifluoroethanol, 2,2,2-trichloroethanol, 2,3-dibromopropanol, 2,3-diiodopropanol, 2,2,3,3,3-pentafluoropropanol, 6,6-dichlorohexanol, 7,8-dibromooctadecanol, 7,8-difluorooctadecanol, 8,9-diiodoeicosanol and the like.

In a more preferred embodiment, the halogen-substituted alcohol is a fluorine-substituted alcohol. In a still more preferred embodiment, the fluorine-substituted alcohol is a mixture of (a) trifluoroethanol and (b) a telomer alcohol which has the general formula:

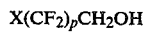

wherein X is hydrogen or fluorine and p is an even integer from 2–12 or mixtures of such telomer alcohol.

In the most preferred embodiment, the fluorine-substituted alcohol is a mixture of about (a) 30–70 wt % trifluoroethanol and (b) about 70–30 wt % of a mixture of telomer alcohols. Most preferably X is hydrogen.

The alcohol reactant can include halogen-free alcohols as well as phenols when the product is desired to contain alkoxides or aryloxides of such alcohols and/or phenols. However, in order for the process to be beneficial the alcohol reactant should contain a substantial amount of halogen-substituted alcohol. For example, alcohol mixtures containing 10 wt % or more halogen-substituted alcohols can benefit from the present process.

The haloalcohol is dissolved in an ether solvent. A wide range of ethers can be used provided they are substantially inert under the reaction conditions. It is highly preferred that the ether solvent also be capable of dissolving the haloalkoxide-substituted polyphosphazene formed when the sodium haloalkoxide is reacted with phosphonitrilic chloride polymer. Useful solvents are diethyl ether, ethyl butyl ether, dibutyl ether, dioxane, dimethoxy ethane, diethoxy ethane, dimethyl ether of diethylene glycol, dibutoxy ethane, dibutyl ether of diethylene glycol. Most work has been carried out using tetrahydrofuran (THF) as the haloalcohol solvent.

The amount of ether solvent should be an amount which will dissolve at least a major portion of the sodium haloalkoxide formed in the reaction. More preferably the amount is sufficient to dissolve substantially all of the sodium haloalkoxide formed in the reaction. The amount required will vary with what ether is selected and what haloalkoxide is prepared. The required amount can be determined experimentally with very little effort. A useful range in which to test is about 300–5000 parts by weight ether for each 100 parts of haloalcohol. A more preferred range is about 350–1000 parts of ether solvent per 100 parts haloalcohol. When making a sodium fluoroalkoxide using the preferred telomer alcohols good results have been achieved with about 300–400 parts THF per 100 parts telomer alcohol.

The sodium dispersion containing allylphenoxides is added to the halogen-substituted alcohol at a rate such that there is not a large amount of unreacted sodium in the halogen-substituted alcohol at any time. The rate of sodium reacting with the alcohol hydroxyl to form alkoxide can be followed by measuring hydrogen evolution. Generally, good results have been obtained by limiting sodium feed such that there is less than 0.02 wt % unreacted sodium in the reaction mixture at any time.

The temperature of the reaction mixture need not be raised. Preferably the reaction temperature is maintained at about −20° to +30° C. Excellent results with no noticeable halogen reaction have been obtained at about −10° to +20° C. The preferred reaction temperature is about −5° up to about 10° C.

The amount of sodium dispersion added to the halogen-substituted alcohol should be an amount which is sufficient to react with most of the alcohol hydroxyl groups. If an excess of sodium dispersion is added to the halogen-substituted alcohol, the amount of alcohol should be sufficient to consume most of the sodium. Preferably, the amount of alcohol should consume at least 90 wt % of the sodium metal in the dispersion. A preferred amount is about 0.8–1.5 equivalent of sodium metal per each equivalent of alcohol hydroxyl. A more preferred range is about 0.9–1.0 equivalents of sodium per alcohol hydroxyl equivalent. Most preferably about one equivalent of sodium is added for each equivalent of alcohol hydroxyl.

Addition time for the sodium dispersion is generally about ten minutes up to about eight hours. The reaction mixture is stirred during this time under an inert atmosphere such as nitrogen. After completion of the addition, the mixture is stirred for a short period up to about two hours. Any unreacted sodium remaining at this time is removed by filtration. The following examples show how the process is conducted.

EXAMPLE 1

In a pressure resistant dispersion vessel equipped with a ¾" diameter turbine-type high shear agitator was placed 273 g of cyclohexane and 170 g of clean sodium. The vessel was flushed with nitrogen and sealed. The vessels contents were heated to about 105° C. to melt the sodium. When the sodium was melted, the agitator was started and 0.7 ml of o-allylphenol was injected into the vessel. The agitator was run thirty minutes at 14,000 rpms and then stopped. The vessel was allowed to cool to 64° at which time it was discharged resulting in a very fine stable sodium dispersion.

In a second reactor was placed 1,490 g of tetrahydrofuran, 182 g of tri-fluoroethanol and 190 g of telomer fluoroalcohols. While stirring under nitrogen at about 0°–5° C. a quantity of the above sodium dispersion which contained about 61 g of sodium metal was fed over 2.6 hours. The mixture was then stirred at 15°–20° C. for 40 minutes to complete the reaction. Less than 1 g of sodium remained unreacted.

EXAMPLE 2

Another dispersion was made similar to Example 1 using 170 g sodium, 274 g cyclohexane and 0.86 g o-allylphenol. A quantity of this dispersion containing about 60 g of sodium metal was fed under nitrogen to a third solution of 180 g of trifluoroethanol, 180 g of telomer fluoroalcohols and 1600 g of tetrahydrofuran at 0°–5° C. over a 120 minute period. No sodium metal was detected following the reaction.

The alkali metal haloalkoxides and allylphenoxides made by the process are used to insert haloalkoxide and allylphenoxide groups on phosphonitrilic chloride polymers (chloropolymers). Chloropolymers are well known compositions and come in a wide range of molecular weights. At one extreme are the low molecular weight cyclic chloropolymers such as phosphonitrilic chloride trimer and tetramer made by the reaction of $PCl_5$ and $NH_4Cl$ in approximately equal mole amounts in a solvent such as monochlorobenzene. Slightly higher molecular weight oligomer products can be made by the same general reaction using a moler excess of $PCl_5$. These oligomers usually contain about 3–9 $(PNCl_2)$ units.

The cyclic chloropolymers can be converted to high molecular weight chloropolymers by heating the purified cyclic chloropolymer to temperatures in the range of about 220°–275° C. The low molecular weight oligomers can be converted to high molecular weight chloropolymers by heating with $NH_4Cl$ at a temperature of about 130°–200° C. as described in U.S. Pat. No. 4,374,815.

Although the sodium haloalkoxides and allylphenoxide mixture made by the present process can be reacted with any chloropolymer to introduce haloalkoxide group, it is preferred that the chloropolymer contain at least about 10 $(PNCl_2)$ units. More preferably, the chloropolymer is a high molecular weight substantially linear chloropolymer containing over 100 $(PNCl_2)$ units and most preferably over 1,000 such units.

The haloalkoxide and allylphenoxide groups are introduced into the chloropolymer by dissolving the chloropolymer in an inert solvent and then adding the ether solution of the haloalkoxide and allylphenoxide. Suitable solvents for the chloropolymer are ethers, aromatics, cycloaliphatics and ketones. Representative examples of such solvents are tetrahydrofuran, diethyl ether, dibutyl ether, dioxane, dimethoxyethane, dimethyl ether of diethylene glycol, benzene, toluene, xylene, cyclopentane, cylcohexane, cycloheptane, cyclooctane, cyclododecane, methylcyclohexane, acetone, methyl ethyl ketone, diethyl ketone, dibutyl ketone and the like. Preferred solvents are tetrahydrofuran, toluene and cyclohexane.

The amount of solvent should be sufficient to dissolve all or most of the chloropolymer at reaction temperature. Generally, a stable solution is obtained using about 10–50 Kg of solvent per Kg of chloropolymer. The high molecular weight polymers are slow to dissolve so require stirring for several hours, preferably at slightly elevated temperatures of about 40°–50° C. Preferably the solvent is maintained under an inert dry nitrogen atmosphere during solvation.

The substitution reaction is conducted at moderate temperatures. A useful temperature range is about 25°–100° C. A more preferred temperature range is about 40°–70° C. The reaction is conducted until the desired degree of substitution is obtained or alternatively until the chloride content of the chloropolymer is reduced to the desired level. The reaction is usually complete in about 4–12 hours.

The amount of sodium haloalkoxide phenoxide solution used should be an amount which contains sufficient sodium haloalkoxide and phenoxide to provide the desired degree of substitution. Generally, the solution contains about 0.8–1.05 moles of sodium haloalkoxide and 0.05–0.2 moles of sodium phenoxide preferably allylphenoxide per equivalent of replaceable chloride in the chloropolymer.

The following examples show how the sodium haloalkoxides and allylphenoxides made according to the present process are used in a substitution reaction with chloropolymer.

EXAMPLE 3

An aliquot of the sodium fluoroalkoxides containing allylphenoxides from Example 2 containing 1 g equivalent of sodium was placed in a reaction vessel fitted with a stirrer and heating means. The vessel was purged with nitrogen. Then a 10 wt % solution containing 54 g of high molecular weight chloropolymer in cyclohexane was pumped into the reaction vessel over a ten minute period. Temperature rose from 25° C. to 48° C. Stirring was continued for six hours at 60° C. At completion, the pH was about 7. Two drops of sulfuric acid was added to lower pH to about 5. Then aqueous sodium chloride solution was added to remove salt. The solvents were steamed distilled leaving a substituted polyphosphazene gum. This gum was dried resulting in 148 g of a useful fluoroalkoxy-substituted polyphosphazene containing sufficient allylphenoxide groups to impart cure properties to the elastomer.

We claim:

1. A process for making a mixture of (i) a sodium alkoxide of a halogen-substituted alcohol containing up to 20 carbon atoms and up to 41 halogen atoms and (ii) a sodium aryloxide wherein said aryloxide is selected from phenoxide, substituted phenoxide wherein the substituents are selected from alkyl, alkoxy, halogen, nitro and allyl, and naphthoxide without excessive reaction of sodium with the halogen substituents, said process comprising:
    (a) dispersing about 1 equivalent of molten metallic sodium in a cycloalkane hydrocarbon having about 5–8 carbon atoms and containing about 0.05–0.2 moles of a phenol selected from phenol, substituted phenols wherein the substituents are selected from alkyl, alkoxy, halogen, nitro and allyl, and naphthol at a pressure high enough to maintain said cycloalkane in the liquid phase above the melting temperature of sodium, (b) cooling the resultant sodium dispersion to a temperature below the melting point of sodium and (c) adding said resultant sodium dispersion to a solution of said halogen-substituted alcohol in an ether solvent at a rate such that there is not a large amount of unreacted sodium in the halogen-substituted alcohol at any time and at a temperature of about −30° C. up to reflux, the amount of said halogen-substituted alcohol being sufficient to react with at least 90 weight percent of the metallic sodium in said resultant sodium dispersion.

2. A process of claim 1 wherein said phenol is a substituted phenol wherein at least one substituent is the allyl group.

3. A process of claim 1 wherein said cycloalkane hydrocarbon is cyclohexane.

4. A process of claim 3 wherein said ether solvent is tetrahydrofuran.

5. A process of claim 3 wherein said halogen-substituted alcohol is a fluorine-substituted alcohol and said allyl-substituted phenol is the compound o-allylphenol.

6. A process of claim 5 wherein said ether solvent is tetrahydrofuran.

7. A process of claim 5 wherein said fluorine-substituted alcohol is a mixture of (a) trifluoroethanol and (b) a telomer alcohol which has the formula:

$$X(CF_2)_p CH_2 OH$$

wherein X is selected from hydrogen and fluorine and p is an even integer from 2–12 and mixtures thereof.

8. A process of claim 7 wherein said ether solvent is tetrahydrofuran.

9. A process of claim 7 wherein X is hydrogen.

10. A process of claim 5 wherein said fluorine substituted alcohol is a mixture (a) about 30–70 wt % trifluoroethanol and (b) about 70–30 wt % of a telomer alcohol having the formulae:

$$X(CF_2)_p CH_2 OH$$

wherein X is hydrogen or fluorine and p is an even integer from 2–12 and mixtures of said telomer alcohols.

11. A process of claim 10 wherein X is hydrogen.

12. A process of claim 11 wherein said ether solvent is tetrahydrofuran.

* * * * *